United States Patent
Bonda et al.

Patent Number: 5,993,789
Date of Patent: Nov. 30, 1999

[54] PHOTOSTABLE SUNSCREEN COMPOSITIONS CONTAINING DIBENZOYLMETHANE DERIVATIVE, E.G., PARSOL® 1789, AND DIESTERS OR POLYESTERS OF NAPHTHALENE DICARBOXYLIC ACID PHOTOSTABILIZERS AND ENHANCERS OF THE SUN PROTECTION FACTOR (SPF)

[75] Inventors: Craig A. Bonda, Wheaton; Peter J. Marinelli, Bartlett; Yin Z. Hessefort, Naperville; Jagdish Trivedi, Woodridge; Gary Wentworth, Chicago, all of Ill.

[73] Assignee: The C.P. Hall Company, Chicago, Ill.

[21] Appl. No.: 09/276,051

[22] Filed: Mar. 25, 1999

[51] Int. Cl.⁶ ............... A61K 7/42; A61K 7/44; A61K 7/00
[52] U.S. Cl. ............... 424/59; 60/400; 60/401
[58] Field of Search ............... 424/59, 60, 400, 424/401

[56] References Cited

U.S. PATENT DOCUMENTS

| | | | |
|---|---|---|---|
| 4,387,089 | 6/1983 | De Polo | 424/59 |
| 4,489,057 | 12/1984 | Welters et al. | 424/47 |
| 4,562,067 | 12/1985 | Hopp et al. | 424/59 |
| 5,670,140 | 9/1997 | Deflandre et al. | 424/59 |
| 5,783,173 | 7/1998 | Bonda et al. | 424/59 |
| 5,788,954 | 8/1998 | Bonda et al. | 424/59 |
| 5,849,273 | 12/1998 | Bonda et al. | 424/59 |
| 5,882,634 | 3/1999 | Allard et al. | 424/59 |

OTHER PUBLICATIONS

"Photostable Cosmetic Light Screening Composition", Author: Anon. Organization, UK Publication Source, Research Disclosure (1999), 418(Feb.), P175 (No. 41803). Identifier–Coden RSDSBB ISSN 0374–4363Publisher Kenneth Mason Publications Ltd. Patent Information.

"Polyester and Copolyester Sheeting, Film and Structured Products Stabilized Against Degradation by Sunlight or Other UV Sources", Author: Anon. Organization, Research Disclosure (1994), (Nov.), P601 (No. 36708).

*Primary Examiner*—Shelley A. Dodson
*Attorney, Agent, or Firm*—Marshall, O'Toole, Gerstein, Murray & Borun

[57] ABSTRACT

A sunscreen composition containing a UV-A dibenzoylmethane derivative, such as 4-(1,1-dimethylethyl)-4'-methoxydibenzoylmethane (PARSOL® 1789), and a stabilizer for the dibenzoylmethane derivative having formula (I) or (II), or mixtures:

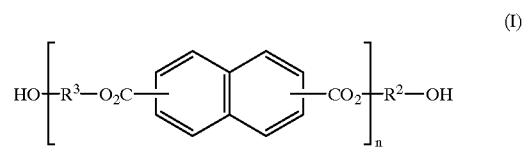

(I)

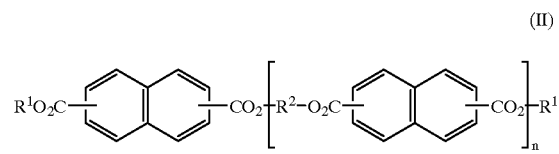

(II)

wherein each $R^1$, same or different, is an alkyl group having 1 to 22 carbon atoms, a diol having the structure $HO—R^2—OH$, or a polyglycol having the structure $HO—R^3—(—O—R^2—)_m—OH$, wherein $R^2$ and $R^3$, same or different, are each an alkylene group, straight chain or branched, having 1 to 6 carbon atoms, and wherein m and n are each 1 to about 100, or a mixture thereof. These diesters and polyesters of formula (I) or (II) are quite effective in stabilizing the dibenzoylmethane derivative UV-A filter compounds making them more effective, and effective for longer periods of time.

20 Claims, 9 Drawing Sheets

PHOTOSTABLE SUNSCREEN COMPOSITIONS CONTAINING DIBENZOYLMETHANE DERIVATIVE, E.G., PARSOL® 1789, AND DIESTERS OR POLYESTERS OF NAPHTHALENE DICARBOXYLIC ACID PHOTOSTABILIZERS AND ENHANCERS OF THE SUN PROTECTION FACTOR (SPF)

FIELD OF THE INVENTION

The present invention is directed to a photostable, broad spectrum (UV-A/UV-B), stable sunscreen composition for topical application to human skin to protect the skin against UV radiation damage. More particularly, the present invention is directed to the use of diesters and/or polyesters of a naphthalene dicarboxylic acid that are surprisingly effective in photostabilizing dibenzoylmethane derivatives, particularly 4-(1,1-dimethylethyl)-4'-methoxydibenzoylmethane (avobenzone or PARSOL® 1789). The diesters and polyesters of naphthalene dicarboxylic acid photostabilize the PARSOL® 1789 and improve the Sun Protection Factor (SPF) to provide a more effective sunscreen composition compared to currently marketed sunscreens having the same or higher levels of UV absorbing active ingredients. This improved performance means the composition maintains its level of effectiveness over a longer period of time and, therefore, need not be applied to the skin as frequently. Other sunscreen agents can be included, such as octyl methoxycinnamate (UV-B), benzophenone 3 (UV-A/UV-B) (a/k/a oxybenzone), octyl salicylate (UV-B), octyl triazone (UV-B), phenylbenzimidazole sulfonic acid (UV-B), methylbenzilidene camphor (UV-A/UV-B), or octocrylene (UV-A/UV-B) to increase the SPF to a value of at least 2, preferably at least 8, while maintaining the stabilization of the dibenzoylmethane derivative UV-A sunscreen agent, e.g., PARSOL 1789.

BACKGROUND OF THE INVENTION AND PRIOR ART

It is well known that ultraviolet light having a wavelength between about 280 nm or 290 nm and 320 nm (UV-B) is harmful to human skin, causing burns that are detrimental to the development of a good sun tan. UV-A radiation, while producing tanning of the skin, also can cause damage, particularly to very lightly colored, sensitive skin, leading to reduction of skin elasticity and wrinkles.

Therefore, a sunscreen composition should include both UV-A and UV-B filters to prevent most of the sunlight within the full range of about 280 nm to about 400 nm from damaging human skin.

The UV-B filters that are most widely used commercially in sunscreen compositions are paramethoxycinnamic acid esters, such as 2-ethylhexyl paramethoxycinnamate, commonly referred to as octyl methoxycinnamate or PARSOL® MCX, having an ethyl radical extending from the 2 position of the hexyl long chain backbone; oxybenzone; and octyl salicylate.

The UV-A filters most commonly used in commercial sunscreen compositions are the dibenzoylmethane derivatives, particularly 4-(1,1-dimethylethyl)-4'-methoxydibenzoylmethane (PARSOL® 1789), and 4-isopropyl dibenzoylmethane (EUSOLEX 8020). Other dibenzoylmethane derivatives described as UV-A filters are disclosed in U.S. Pat. Nos. 4,489,057; 4,387,089 and 4,562,067 and 5,670,140, hereby incorporated by reference. It is also well known that the above described and most commonly used UV-A filters, particularly the dibenzoylmethane derivatives, such as PARSOL® 1789, suffer in photochemical stability when used alone or in combination with the above-described most commercially used UV-B filters. Accordingly, when used alone or when combined with a UV-B filter, such as 2-ethylhexyl paramethoxycinnamate (PARSOL® MCX), oxybenzone and/or octyl salicylate, the PARSOL® 1789 becomes less photochemically stable necessitating repeated, frequent coatings over the skin for sufficient UV radiation protection.

In accordance with the principles of the present invention, it has been found, quite surprisingly, that by including a diester and/or polyester of one or more naphthalene dicarboxylic acids of formula (I), into a cosmetic sunscreen formulation containing a UV-A dibenzyolmethane derivative, particularly PARSOL® 1789, and/or 4-isopropyl dibenzoylmethane (EUSOLEX 8020), the dibenzyolmethane derivative is photochemically stabilized so that the dibenzyolmethane derivative-containing sunscreen composition with or without additional sunscreen agents, such as oxybenzone and/or octyl methoxycinnamate (ESCALOL 567), is more effective for filtering out UV-A radiation; the composition filters more UV-A radiation for longer periods of time; and, therefore, the sunscreen formulation need not be applied to the skin as frequently while maintaining effective skin protection against UV-A radiation.

In accordance with another important advantage of the present invention, it has been found that the diesters and polyesters of naphthalene dicarboxylic acids can also absorb UV light in the most damaging range of about 280–300 nm, especially over the 280 and 295 nm wavelength absorbance peaks shown in FIG. 9, to further boost the SPF of the sunscreen compositions.

By the addition of UV-B filter compounds, such as octyl methoxycinnamate, octyl salicylate, and/or oxybenzone, the cosmetic sunscreen formulation can maintain surprisingly effective skin protection against UV radiation both in the UV-A and UV-B range, with or without common sunscreen additives, such as octocrylene, and/or titanium dioxide. The composition reaches a surprisingly high SPF without solid additives, such as titanium dioxide, thereby providing an exceptionally elegant feel that can be applied easily in a continuous coating for complete coverage and sunscreen protection. The ratio of UV-A to UV-B filter compounds is in the range of about 0.1:1 to about 3:1, preferably about 0.1:1 to about 0.5:1, most preferably about 0.3:1 to about 0.5:1. Quite surprisingly, the preferred compositions of the present invention achieve unexpectedly high SPF, e.g., higher than SPF 12 in one preferred composition, and higher than SPF 20 in another preferred composition, with the addition of surprisingly low amounts of other UV-B and UV-A filters to the PARSOL 1789, and without solid blocking compounds, such as $TiO_2$.

SUMMARY OF THE INVENTION

In brief, the present invention is directed to sunscreen compositions containing a dibenzoylmethane derivative UV-A filter compound, such as 4-(1,1-dimethylethyl)-4'-methoxydibenzoylmethane (PARSOL® 1789), and a diester and/or polyester of a naphthalene dicarboxylic acid that photostabilizes the dibenzoylmethane derivative.

The present photostabilizers are diesters and polyesters of a naphthalene dicarboxylic acid. The esters and polyesters are reaction products of (a) a naphthalene dicarboxylic acid having the structure:

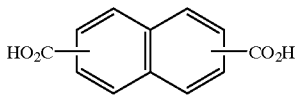

and (b) an alcohol having the structure $R^1$—OH, or a diol having the structure HO—$R^2$—OH, or a polyglycol having the structure HO—$R^3$—(—O—$R^2$—)$_m$—OH, wherein $R^1$ is an alkyl group, straight chain or branched, having 1 to 22 carbon atoms, $R^2$ and $R^3$, same or different, are each an alkylene group, having 1 to 6 carbon atoms, and wherein m and n are each 1 to about 100, preferably 1 to about 10, more preferably 2 to about 7, or a mixture thereof.

A diester of the present invention has the structure:

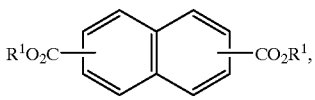

wherein $R^1$ is as defined above.

The diesters and polyesters of naphthalene dicarboxylic acids that photostabilize the dibenzoylmethane derivatives have the general formula (I):

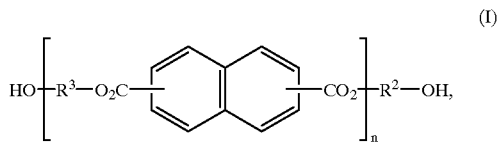

wherein $R^2$ and $R^3$, same or different, are each an alkylene group having 1 to 6 carbon atoms, and n=1 to about 100, preferably 1 to about 10, more preferably 2 to about 7.

Alternatively, the photostabilizing diesters and polyesters of the present invention can be end-capped with an alcohol or an acid. The end-capped polyesters have the structural formula (II):

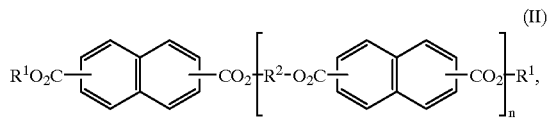

wherein $R^1$ and $R^2$ and n are as defined above, with reference to formula (I). The two $R^1$s in formula (II) may be the same or different.

The preferred diesters and polyesters of the present invention have a weight average molecular weight of about 244 to about 4000, and more preferably about 450 to about 1500. To achieve the full advantage of the present invention, the diester or polyester has a weight average molecular weight of about 500 to about 1000.

The naphthalene dicarboxylic acid is selected from the group consisting of 1,2-naphthalene dicarboxylic acid; 1,3-naphthalene dicarboxylic acid; 1,4-naphthalene dicarboxylic acid; 1,5-naphthalene dicarboxylic acid; 1,6-naphthalene dicarboxylic acid; 1,7-naphthalene dicarboxylic acid; 1,8-naphthalene dicarboxylic acid; 2,3-naphthalene dicarboxylic acid; 2,6-naphthalene dicarboxylic acid; 2,7-naphthalene dicarboxylic acid, and mixtures thereof. Preferred dicarboxylic acids are the 2,6-, 1,5- and 1,8-naphthalene dicarboxylic acids.

The alcohol $R^1$—OH can be, for example, methanol, ethanol, propanol, isopropyl alcohol, n-butanol, sec-butanol, isobutyl alcohol, tert-butyl alcohol, amyl alcohol, 1-hexanol, 1-octanol, 1-decanol, isodecyl alcohol, 1-undecanol, 1-dodecanol, 1-tridecyl alcohol, 1-tetradecanol, 1-hexadecanol, 1-octadecanol, 1-eicosonol, 1-decosonol, 2-ethylhexyl alcohol, 2-butyloctanol, 2-butyldecanol, 2-hexyldecanol, 2-octyldecanol, 2-hexyldodecanol, 2-octyldodecanol, 2-decyltetradecanol, and mixtures thereof.

The glycol or polyglycol can be, for example, ethylene glycol, propylene glycol, 1,2-propanediol, diethylene glycol, triethylene glycol, tetraethylene glycol, dipropylene glycol, tripropylene glycol, methyl propanediol, 1,6-hexanediol, 1,3-butanediol, 1,4-butanediol, PEG-4 through PEG-100, PPG-9 through PPG-34, pentylene glycol, neopentyl glycol, trimethylpropanediol, 1,4-cyclohexanedimethanol, 2,2-dimethyl-1,3-propanediol, 2,2,4,4-tetramethyl-1,3-cyclobutanediol, and mixtures thereof.

Surprisingly, it has been found that these diesters and polyesters of naphthalene dicarboxylic acids are quite effective in stabilizing the dibenzoylmethane derivative UV-A filter compounds making them more effective; effective for longer periods of time; and, therefore, the sunscreen composition need not be reapplied as frequently to maintain effective UV radiation skin protection.

Accordingly, one aspect of the present invention is to provide a stable sunscreen composition that includes a diester or polyester of one or more naphthalene dicarboxylic acids as a photostabilizer compound, said naphthalene dicarboxylic acid diester/polyester photostabilizers having formula (I) or (II), being capable of stabilizing a dibenzoylmethane derivative UV-A filter, particularly PARSOL® 1789.

Another aspect of the present invention is to provide photochemical stabilizer compounds for dibenzoylmethane derivatives, particularly PARSOL® 1789, and methods of manufacturing the stabilizer compounds, capable of stabilizing the dibenzoylmethane derivatives, and capable of increasing the sunscreen protection factor (SPF) achievable for sunscreen compositions containing the dibenzoylmethane derivatives to a SPF of at least 2, particularly higher than SPF 8.

Another aspect of the present invention is to provide a stable sunscreen composition that has a SPF of at least 12, preferably at least about 20, without a sunscreen composition additive selected from the group consisting of octocrylene or camphor derivatives such as methylbenzilidene camphor or substituted dialkylbenzalmalonates or substituted dialkylmalonates, or solid blocking agents such as $TiO_2$ or zinc oxide. It should be understood however, that these sunscreen composition additives can be included in the composition of the present invention without detrimental effect.

Another aspect of the present invention is to provide an improved, stable sunscreen composition containing a diester and/or polyester of a naphthalene dicarboxylic acid that increases the effectiveness of dibenzoylmethane derivative sunscreen compounds, particularly 4-(1,1-dimethylethyl)-4'-methoxydibenzoylmethane (PARSOL® 1789), in SPF and in duration.

Another aspect of the present invention is to provide a stable, broad spectrum sunscreen composition that has a SPF of at least 12 and provides substantial protection against the full range of solar UV radiation (280–400 nm), including about 4–15% by weight of an ester and/or polyester of naphthalene dicarboxylic acid, and contains less than 7% and preferably less than 6.1% of sunscreen composition additives selected from the group oxybenzone and avobenzone (PARSOL 1789).

Still another aspect of the present invention is to provide a sunscreen composition containing a combination of acrylate/$C_{10-30}$ alkyl acrylate block copolymers, e.g., PEMULEN TR-1 and PEMULEN TR-2, in a weight ratio of TR-1 less than, equal to, or greater than TR-2, preferably in a weight ratio of 1:1 to 3:1 TR-1:TR-2, more preferably about 1:1 to 2:1, in a combined amount of at least 25% by weight, preferably at least 30% by weight, for use in emulsification of the oil phase, and increased viscosity, while maintaining a completely non-greasy after feel. The more hydrophobic PEMULEN TR-2 include a molar ratio of $C_{10-30}$ alkyl acrylate to acrylate of about twice as high as the ratio of $C_{10-30}$ alkyl acrylate to acrylate of PEMULEN TR-1 to provide more hydrophobicity and better oil emulsification.

It has been found that the acrylate/$C_{10-30}$ alkyl acrylate crosspolymers in a preferred weight ratio of 1:1–2:1 TR-1:TR:2 emulsify the compositions of the present invention such that the composition can be spread over the skin without gas bubbles or voids while providing a non-greasy after feel, and providing sufficient viscosity, and complete emulsification of the oil phase of the composition so that complete coverage of the skin is achieved, without interfering with the high SPF provided by the sunscreen and stabilizer compounds of the composition.

Still another aspect of the present invention is to provide a moisturizing sunscreen composition that provides an SPF of at least 20, including about 4–15% by weight of an ester and/or polyester of naphthalene dicarboxylic acid, and contains less than 5.1%, preferably about 1–3% by weight PARSOL® 1789 and less than a total of 7% by weight, preferably about 6% by weight or less of sunscreen composition additives selected from the group consisting of octyl methoxycinnamate, oxybenzone, octyl triazone, and octyl salicylate, preferably 2% by weight or less octyl methoxycinnamate and 4% by weight or less oxybenzone.

The above and other aspects and advantages of the present invention will become more apparent from the following detailed description of the preferred embodiments, taken in conjunction with the drawings.

DETAILED DESCRIPTION OF THE PREFERRED EMBODIMENTS

The sunscreen compositions of the present invention include about 0.5% to about 5%, preferably about 0.5% to about 3% of a dibenzoylmethane derivative UV-A filter compound, such as 4-(1,1-dimethylethyl)-4'-methoxy-dibenzoylmethane (PARSOL® 1789) and about 1% to about 10% by weight of a diester and/or polyester of one or more naphthalene dicarboxylic acid photostabilizer/solubilizer for the dibenzoylmethane derivative, having formula (I) or (II).

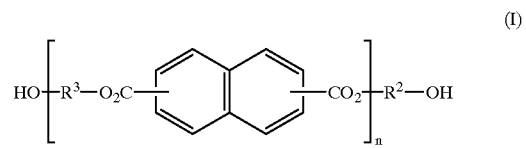

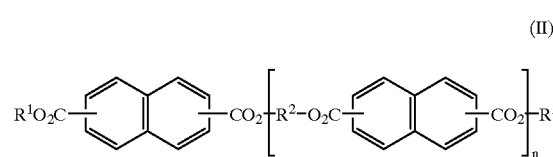

wherein each $R^1$, same or different, is an alkyl group having 1 to 22 carbon atoms, or a diol having the structure HO—$R^2$—OH, or a polyglycol having the structure HO—$R^3$—(—O—$R^2$—)$_m$—OH, and, wherein $R^2$ and $R^3$, same or different, are each an alkylene group, straight chain or branched, having 1 to 6 carbon atoms, wherein m and n are each 1 to about 100, preferably 1 to about 10, more preferably 2 to about 7, or a mixture thereof.

The compounds of formula (I) and (II) are well known for other purposes.

EXAMPLES

Example 1

The photostabilizing effect of a polyester of 2,6-naphthalene dicarboxylic acid and tripropylene glycol with a 2-butyloctanol terminator was determined as follows. First, the following formulations containing 1% PARSOL® 1789 were prepared in the usual way by dissolving the PARSOL® 1789 in the oily phase and premixing the water phase, then emulsifying the oil by adding it to the water phase:

| Ingredient | Formula A (Standard) | Formula B | Formula C | Function |
|---|---|---|---|---|
| hexyldecyl benzoate & butyloctyl benzoate | 7.50% | 7.50% | 7.50% | emollient, solvent |
| isopropyl myristate | 5.00% | 5.00% | 1.00% | co-solvent |
| avobenzone | 1.00% | 1.00% | 1.00% | UV-A sunscreen |
| myristyl myristate | 4.00% | 0.00% | 0.00% | bodying agent |
| polyester of 2,6-naphthalene dicarboxylic acid | 0.00% | 4.00% | 8.00% | photostabilizer |
| sorbitan oleate | 0.20% | 0.20% | 0.20% | particle size reducer |
| dimethicone copolyol | 0.10% | 0.10% | 0.10% | lubricant |
| carbomer | 0.20% | 0.20% | 0.20% | thickener, stabilizer |
| acrylates/C10-30 alkyl acrylates crosspolymer | 0.25% | 0.25% | 0.25% | emulsifier |
| deionized water | Q.S. | Q.S. | Q.S. | solvent, carrier |
| disodium EDTA | 0.05% | 0.05% | 0.05% | chelator |
| hydroxypropyl-methylcellulose | 0.20% | 0.20% | 0.20% | film former |
| glycerin | 4.00% | 4.00% | 4.00% | humectant |
| butylene glycol | 2.00% | 2.00% | 2.00% | humectant, solvent |
| phenoxyethanol & parabens | 0.50% | 0.50% | 0.50% | preservative |
| triethanolamine | 0.45% | 0.45% | 0.45% | neutralizer |

The photostability of the PARSOL® 1789 was determined by spreading measured amounts of the emulsions on 5 cm square slides of Vitro-skin, then irradiating the slides with a solar simulator. Absorbance measurements in the UV-A range (315–380 nm) were taken by a Labsphere UV Transmittance Analyzer before and after irradiation and the results compared.

Figure 1:
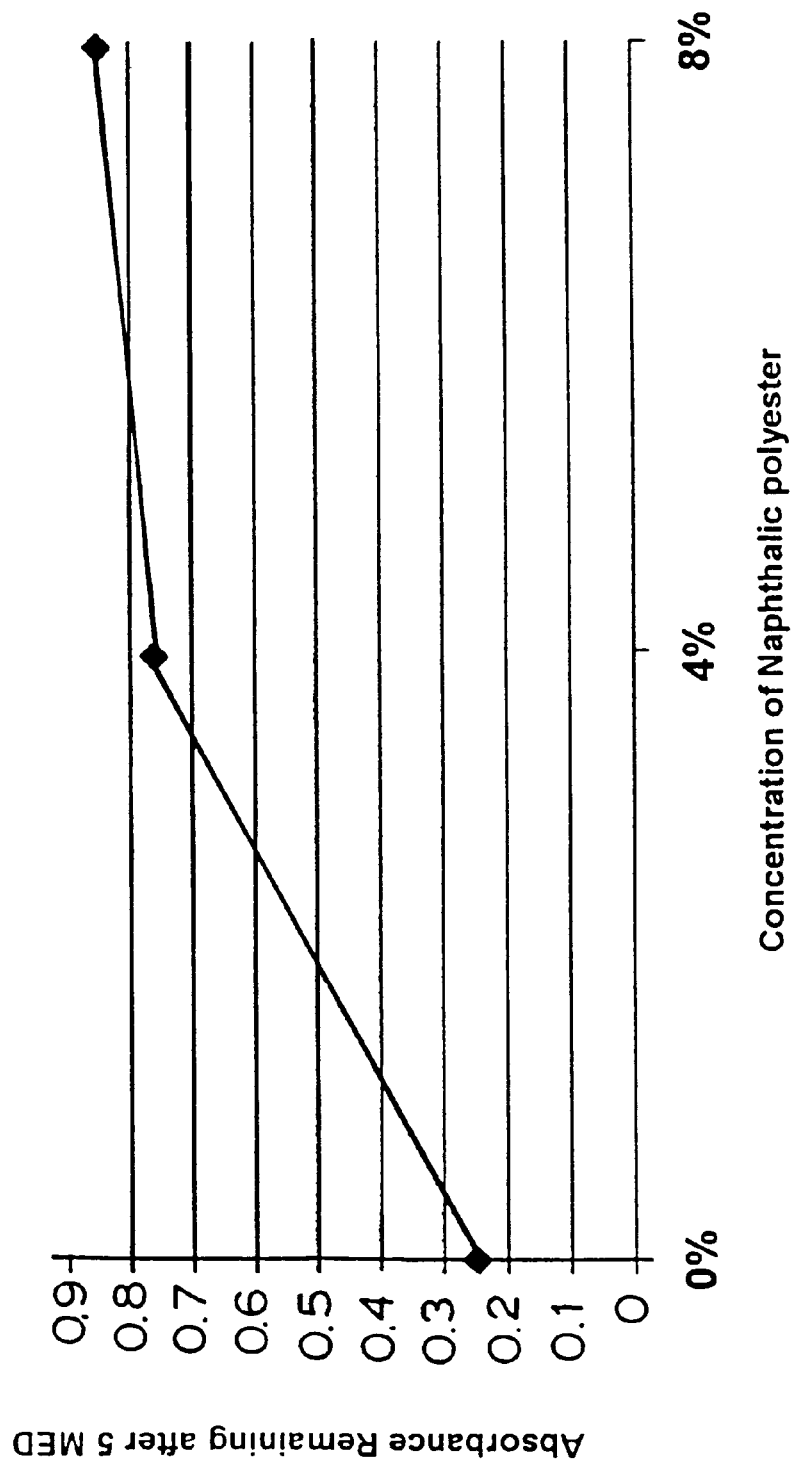
FIG. 1 is a graph showing the photostability of PARSOL® 1789 or 4-(1,1-dimethylethyl)-4'-methoxydibenzoylmethane as a function of concentration of the naphthalene dicarboxylic acid ester photostabilizers of the present invention.
Figure 2:
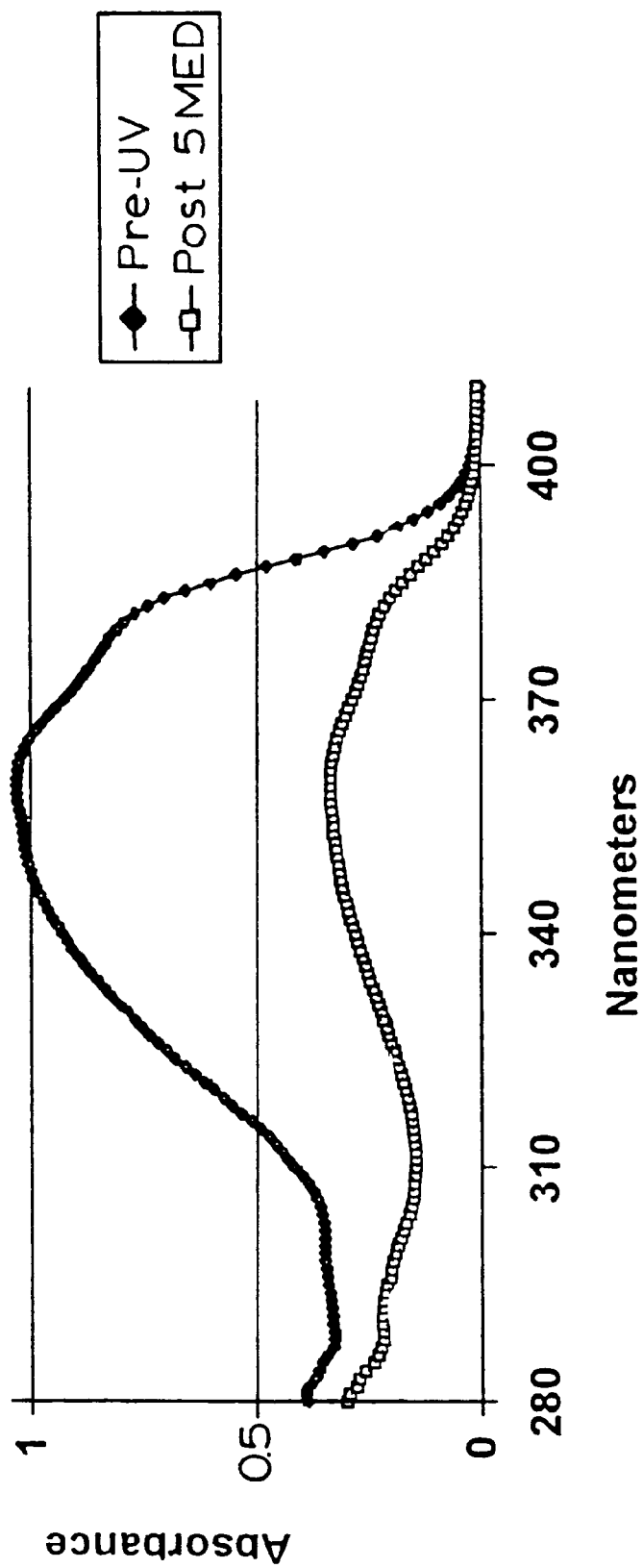
FIG. 2 is a graph showing the photostability (photoinstability) or UV absorbance capability, of a sunscreen composition containing 1% by weight avobenzone when subjected to ultraviolet light of varying wavelengths.
Figure 3:
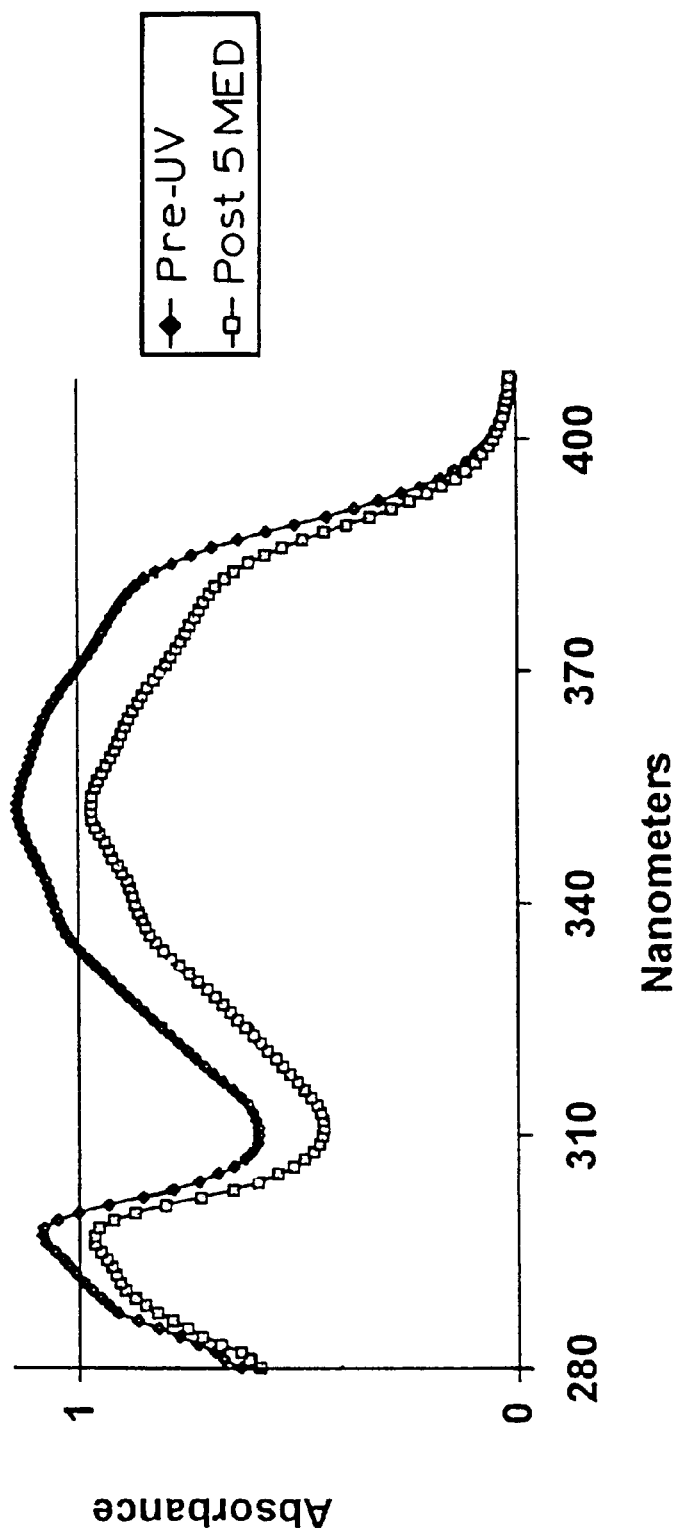
FIG. 3 is a graph showing photostability, or UV absorbance capability, of a sunscreen compositing containing 1% by weight avobenzone when stabilized with 4% by weight of one of the naphthalene dicarboxylic acid polyesters of the present invention.
Figure 4:
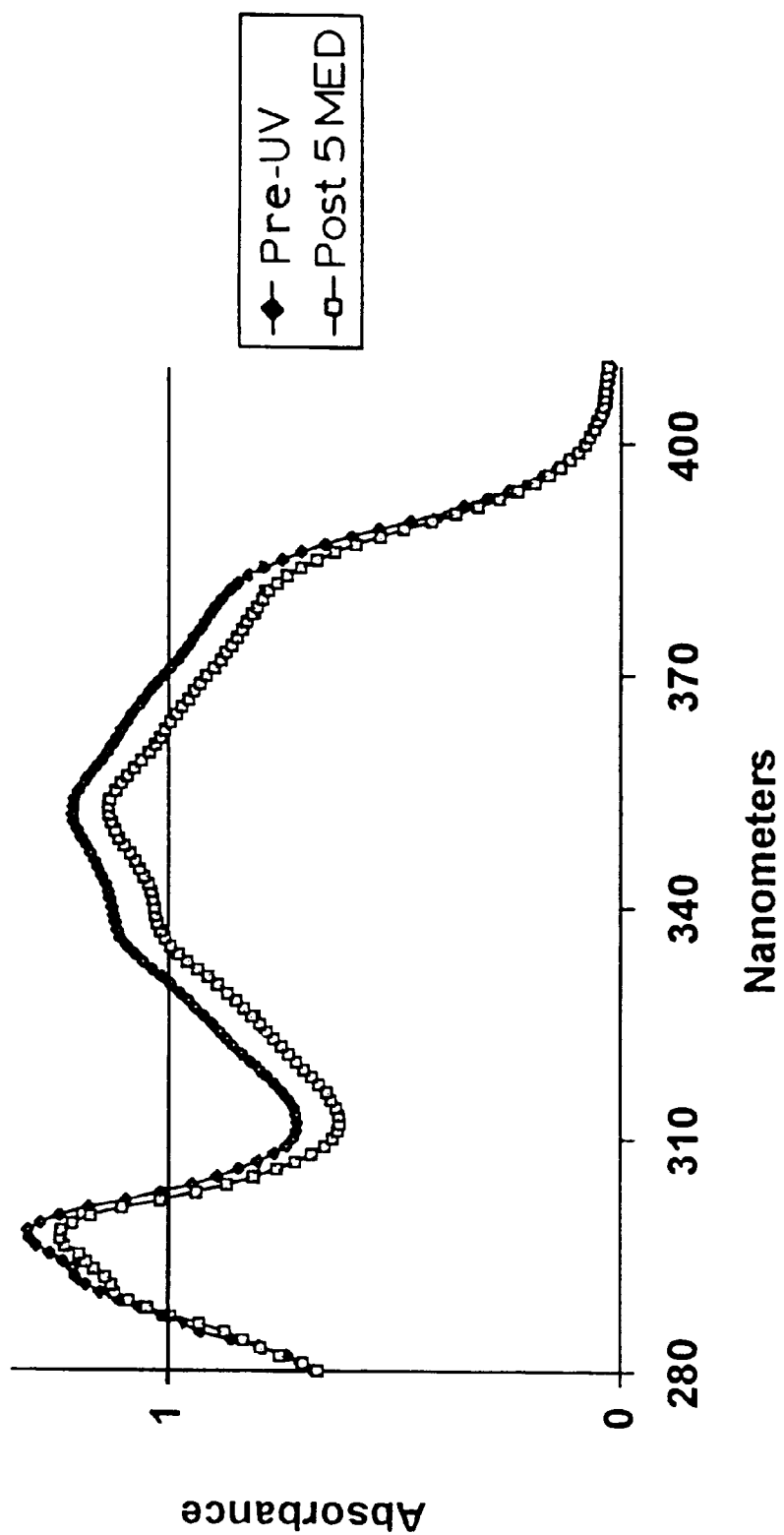
FIG. 4 is a graph showing photostability, or UV absorbance capability, of a sunscreen composition containing 1% by weight avobenzone when stabilized with 8% by weight of one of the naphthalene dicarboxylic acid polyesters of the present invention.
Figure 5:
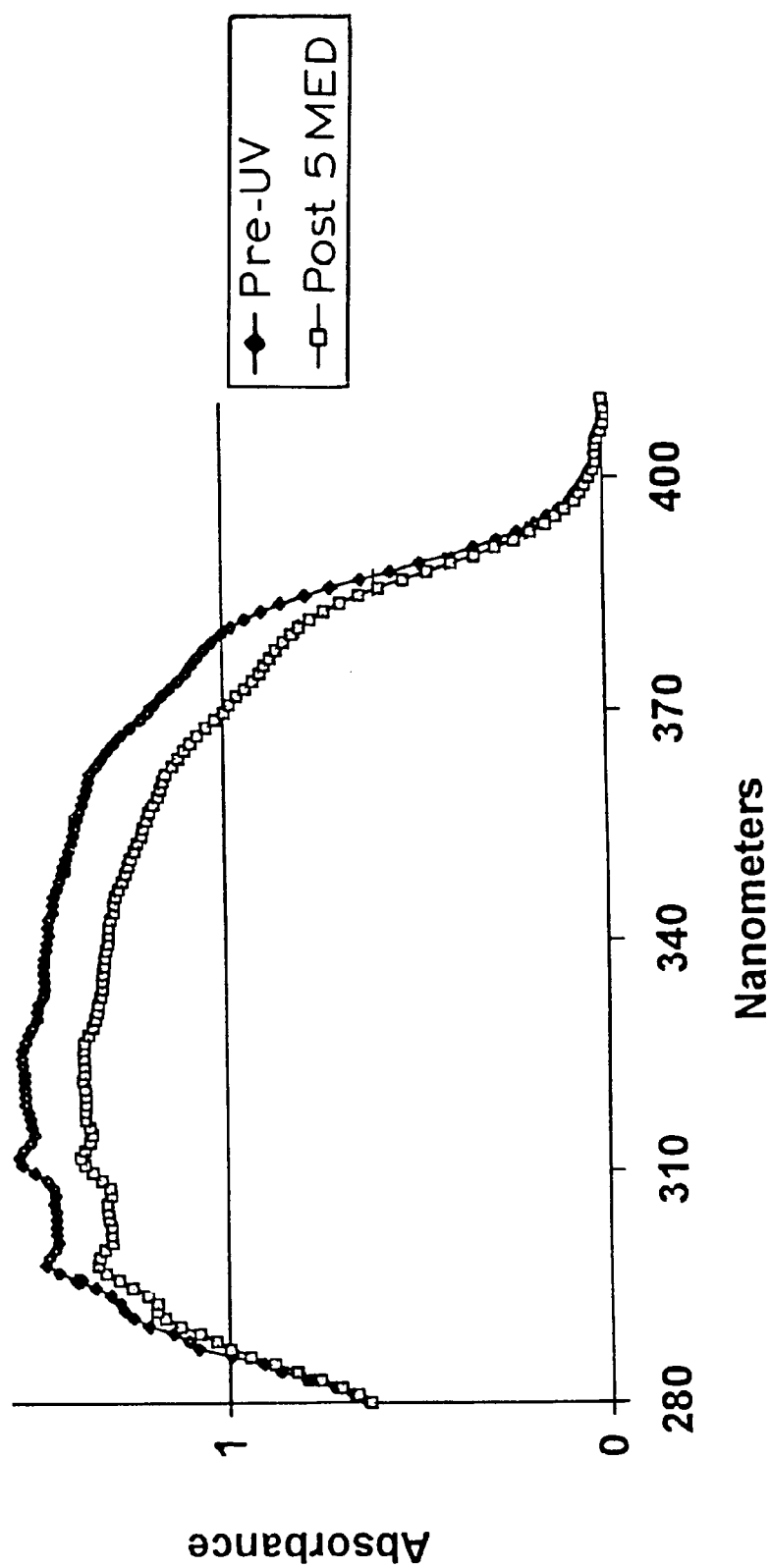
FIG. 5 is a graph showing the photostability of a sunscreen composition containing 3% by weight oxybenzone/1% by weight avobenzone, without a photostabilizer of the present invention.
Figure 6:
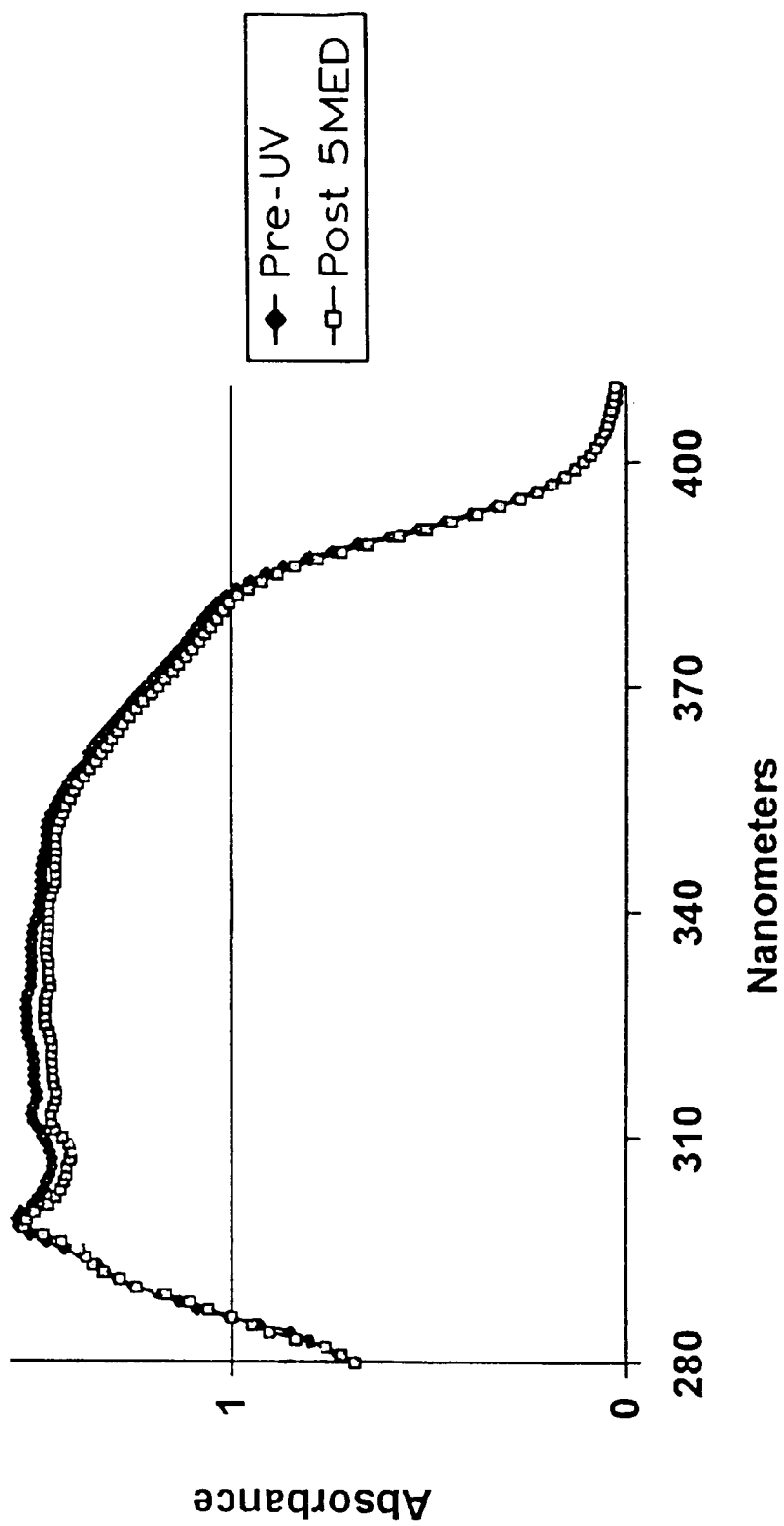
FIG. 6 is a graph showing the photostability of a sunscreen composition containing 3% by weight oxybenzone/1% by weight avobenzone, and 8% by weight of one of the naphthalene dicarboxylic acid polyester photostabilizers of the present invention.
Figure 7:
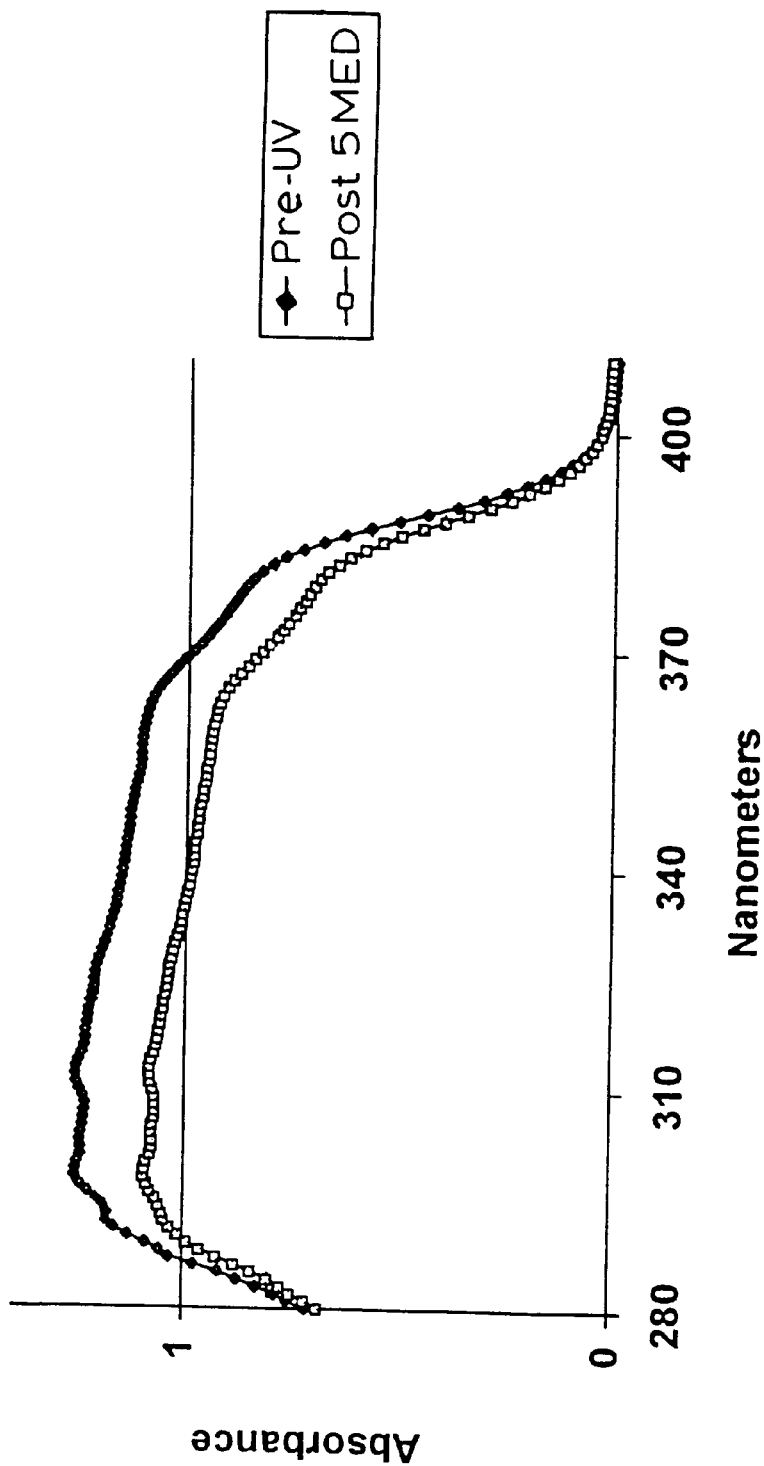
FIG. 7 is a graph showing the photostability of a sunscreen composition containing 1% by weight avobenzone and 4% by weight of an octocrylene photostabilizer.
Figure 8:
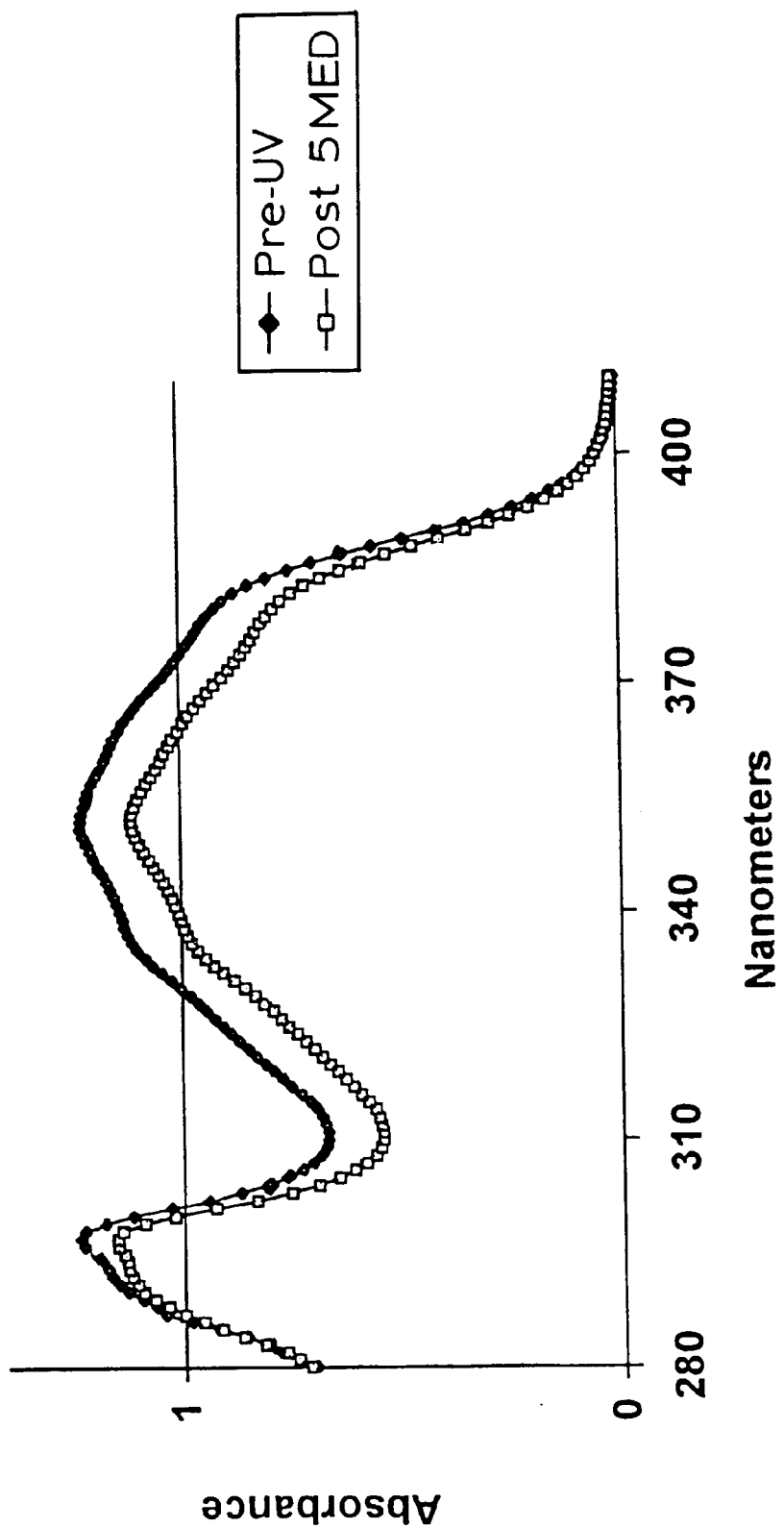
FIG. 8 is a graph showing the photostability of a sunscreen composition containing 1% by weight avobenzone and 4% by weight of an oligomer (MW=~1500) of a naphthalene dicarboxylic acid ester of the present invention.
Figure 9:
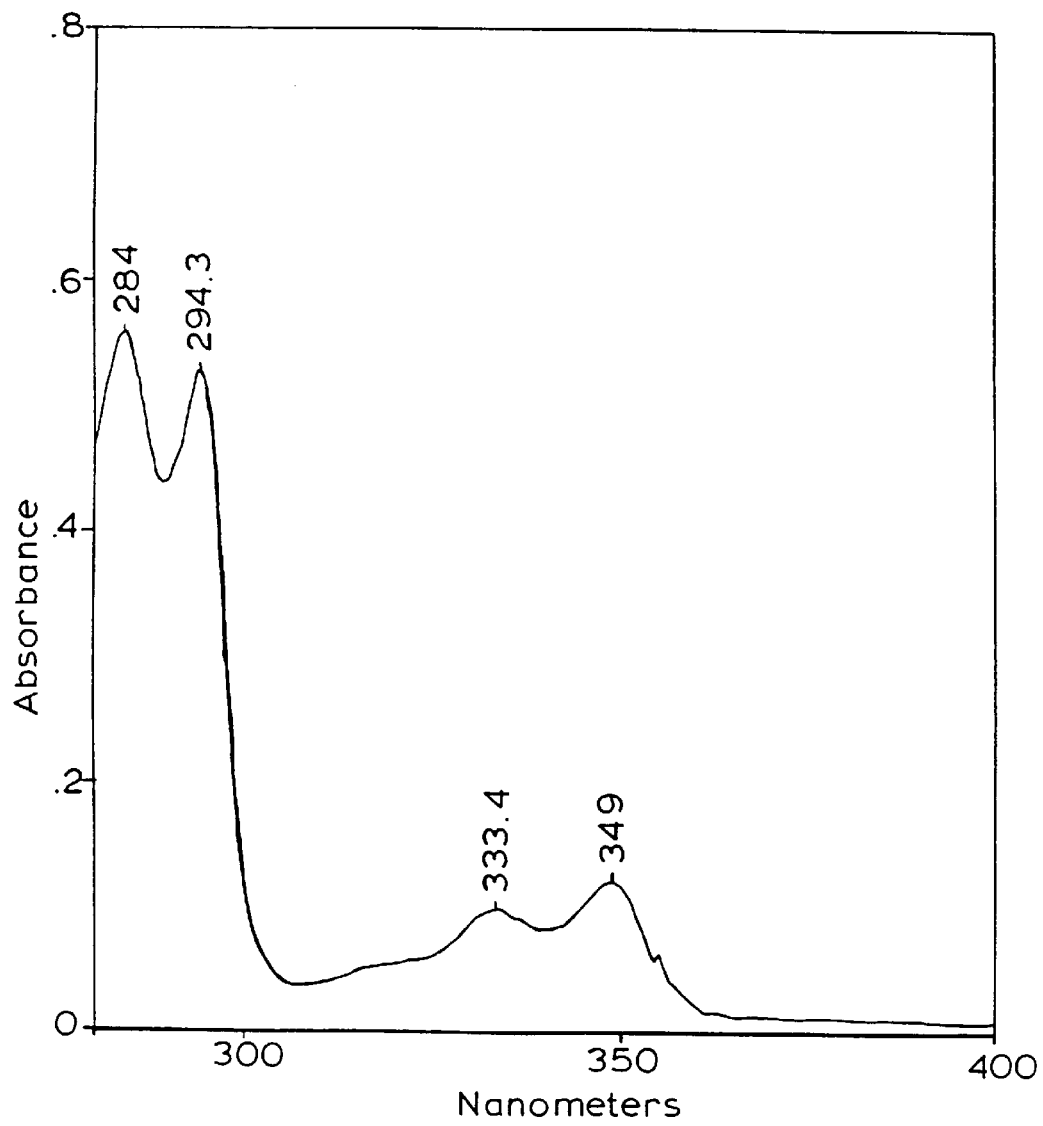
FIG. 9 is a graph showing the UV absorbance of the naphthalic dicarboxylic acid of Example 1 at 17.5 ppm in tetrahydroforan (THF).

After irradiation with 5 MED (minimal erythermal dose), the loss of UV-A absorbance by the PARSOL® 1789 was considerably lower in the formulations containing the PARSOL® 1789 in combination with 4% and 8% of the naphthalene dicarboxylic polymer when compared to the formulation containing the PARSOL® 1789 alone (compare FIGS. 2, 3 and 4). Further, the loss of absorbance in the UV-A range is reduced in a manner related to the concentration of the naphthalene dicarboxylic polymer, as can be seen in the graph of FIG. 1.

Example 2

The photostabilizing effect of a polyester of 2,6-naphthalene dicarboxylic acid, tripropylene glycol, and diethylene glycol with a 2-ethylhexanol terminator was compared to octocrylene, a well known photostabilizer for PARSOL® 1789. The following formulations were prepared in the usual manner, each containing 1% PARSOL® 1789 and 4% of either octocrylene or a polyester of 2,6-naphthalene dicarboxylic acid:

| Ingredient | Formula A | Formula B | Function |
|---|---|---|---|
| hexyldecyl benzoate & butyloctyl benzoate | 7.50% | 7.50% | emollient, solvent |
| isopropyl myristate | 5.00% | 5.00% | co-solvent |
| avobenzone | 1.00% | 1.00% | UV-A sunscreen |
| octocrylene | 4.00% | 0.00% | UV-B/UV-A sunscreen |
| polyester of 2,6-naphthalene dicarboxylic acid | 0.00% | 4.00% | photostabilizer |
| sorbitan oleate | 0.20% | 0.20% | particle size reducer |
| dimethicone copolyol | 0.10% | 0.10% | lubricant |
| carbomer | 0.20% | 0.20% | thickener, stabilizer |
| acrylates/C10-30 alkyl acrylates crosspolymer | 0.25% | 0.25% | emulsifier |
| deionized water | Q.S. | Q.S. | solvent, carrier |
| disodium EDTA | 0.05% | 0.05% | chelator |
| hydroxypropylmethylcellulose | 0.20% | 0.20% | film former |
| glycerin | 4.00% | 4.00% | humectant |
| butylene glycol | 2.00% | 2.00% | humectant, solvent |
| phenoxyethanol & parabens | 0.50% | 0.50% | preservative |
| triethanolamine | 0.45% | 0.45% | neutralizer |

After following the protocol described above in Example 1, the following results were obtained:

| | Formula A | Formula B |
|---|---|---|
| Average loss of UV-A | 26.33% | 22.36% |
| Average loss of UV-B | 25.15% | 18.29% |
| Average loss of SPF | 26.82% | 20.35% |

The test demonstrated that the naphthalene dicarboxylic acid derived polyester is comparable to octocrylene in its ability to photostabilize PARSOL® 1789.

What is claimed is:

1. A sunscreen composition having an SPF of at least 2, for topical application to human skin for protection against ultraviolet radiation comprising, in a cosmetically acceptable carrier, at least about 0.5% by weight of a dibenzoylmethane derivative and at least about 0.5% by weight of a diester or polyester of naphthalene dicarboxylic acid selected from the group consisting of formula (I), formula (II) and mixtures thereof:

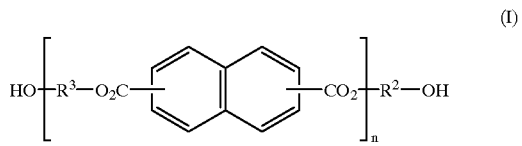

(I)

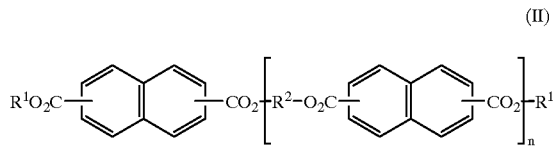

(II)

wherein each $R^1$, some or different, is selected from the group consisting of an alkyl group having 1 to 22 carbon atoms; a diol having the structure $HO-R^2-OH$; and a polyglycol having the structure $HO-R^3-(-O-R^2-)_m-OH$, wherein $R^2$ and $R^3$, same or different, are each an alkylene group, straight chain or branched, having 1 to 6 carbon atoms, and wherein m and n are each in the range of 1 to about 100, or a mixture thereof.

2. A composition in accordance with claim 1, wherein the molar ratio of said stabilizing compound having formula (I) or (II) to said dibenzoylmethane derivative is about 0.1:1 to about 10:1.

3. A composition in accordance with claim 1, wherein the molar ratio of said stabilizing compound having formula (I) or (II) to said dibenzoylmethane derivative is about 0.1:1 to about 0.3:1.

4. A composition in accordance with claim 3, wherein said dibenzoylmethane derivative is selected from the group consisting of 4-(1,1-dimethylethyl)-4'-methoxydibenzoylmethane; 4-isopropyl dibenzoylmethane; and mixtures thereof.

5. A composition in accordance with claim 4, wherein the dibenzoylmethane derivative is 4-(1,1-dimethylethyl)-4'-methoxydibenzoylmethane.

6. A composition in accordance with claim 5, wherein the dibenzoylmethane derivative is included in the composition in an amount of about 0.5% to about 5% by weight of the composition.

7. A composition in accordance with claim 6, wherein the dibenzoylmethane derivative is included in the composition in an amount of about 0.5% to about 3% by weight of the composition.

8. A composition in accordance with claim 7, wherein the stabilizing compound is included in the composition in an amount of about 1% to about 20% by weight of the composition.

9. A composition in accordance with claim 7, wherein the stabilizing compound is a polyester of 2,6-naphthalene dicarboxylic acid.

10. A method of filtering out ultraviolet radiation from human skin comprising topically applying to said skin a composition, in a cosmetically acceptable carrier, comprising 0.5% to 5% by weight of a dibenzoylmethane derivative and a diester or polyester of a naphthalene dicarboxylic acid stabilizing compound selected from the group consisting of formula (I), formula (II) and mixtures thereof:

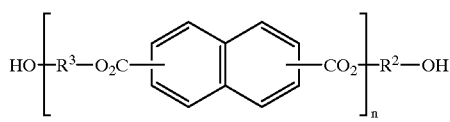

(I)

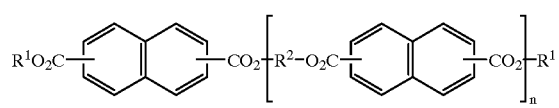

(II)

wherein each $R^1$, same or different, is selected from the group consisting of an alkyl group having 1 to 22 carbon atoms; a diol having the structure $HO-R^2-OH$; and a polyglycol having the structure $HO-R^3-(-O-R^2-)_m-OH$, wherein $R^2$ and $R^3$, same or different, are each an alkylene group, straight chain or branched, having 1 to 6 carbon atoms, and wherein m and n are each in the range of 1 to about 100, or a mixture thereof.

11. A method in accordance with claim 10, wherein the molar ratio of said stabilizing compound having formula (I) or (II) to said dibenzoylmethane derivative is about 0.1:1 to about 10:1.

12. A method in accordance with claim 10, wherein the molar ratio of said stabilizing compound having formula (I) to said dibenzoylmethane derivative is about 0.1:1 to about 0.3:1.

13. A method in accordance with claim 12, wherein said dibenzoylmethane derivative is selected from the group consisting of 4-(1,1-dimethylethyl)-4'-methoxydibenzoylmethane; 4-isopropyl dibenzoylmethane; and mixtures thereof.

14. A method in accordance with claim 13, wherein the dibenzoylmethane derivative is 4-(1,1-dimethylethyl)-4'-methoxydibenzoylmethane.

15. A method in accordance with claim 14, wherein the dibenzoylmethane derivative is included in the composition in an amount of about 0.5% to 3% by weight of the composition.

16. A method of filtering out ultraviolet radiation from human skin comprising topically applying to said skin, in a cosmetically acceptable carrier, a diester or polyester of a naphthalene dicarboxylic acid compound selected from the group consisting of formula (I), formula (II) and mixtures thereof:

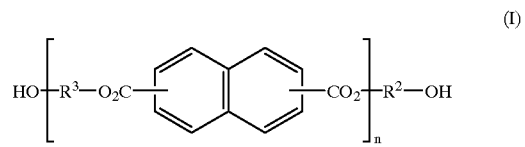

(I)

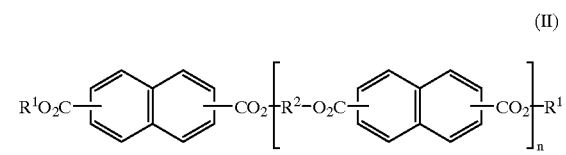

(II)

wherein each $R^1$, same or different, is selected from the group consisting of an alkyl group having 1 to 22 carbon atoms; a diol having the structure $HO-R^2-OH$; and a polyglycol having the structure $HO-R^3-(-O-R^2-)_m-OH$, wherein $R^2$ and $R^3$, same or different, are each an alkylene group, straight chain or branched, having 1 to 6 carbon atoms, and wherein m and n are each in the range of 1 to about 100, or a mixture thereof.

17. A sunscreen composition including the stabilizer defined in claim 1, having the following composition:

| Chemical Name | % W/W |
| --- | --- |
| Dibenzoylmethane derivative | 1–10 |
| Stabilizer of claim 1 | 1–15 |
| Octocrylene | 0–10 |
| Hexyldecyl benzoate & Butyloctyl benzoate | 0–10 |
| UV-A/UV-B sunscreen #1 | 0–10 |
| UV-A/UV-B sunscreen #2 | 0–10 |
| UV-A/UV-B sunscreen #3 | 0–10 |
| UV-A/UV-B sunscreen #4 | 0–10 |
| Dimethicone copolyol | 0–2 |
| Isopropyl myristate | 0–5 |
| Oxybenzone | 0–8 |
| Thickener | 0–2 |
| Sorbitan oleate | 0–5 |
| Acrylate/$C_{10-30}$ alkyl acrylate crosspolymer | 0–5 |
| Water | 50–90 |
| Carbomer | 0–2 |
| Disodium EDTA | 0–2 |

| Chemical Name | % W/W |
|---|---|
| Glycerin | 0–10 |
| Butylene glycol | 0–5 |
| Phenoxyethanol()methyl-paraben()ethylparaben()propylparaben()butylparaben | 0–5 |
| Chlorphenisen | 0–5 |

18. The sunscreen composition of claim 17 having the following composition:

| Chemical Name | % W/W |
|---|---|
| 4-(1,1-dimethylethyl)-4'-methoxydibenzoylmethane | 1–10 |
| Stabilizer of claim 1 | 1–15 |
| Butyloctyl salicylate | 5–10 |
| UV-A/UV-B sunscreen | 0.5–10 |
| Water | 50–90 |

19. A sunscreen composition including the stabilizer defined in claim 1, having the following composition:

| Chemical Name | % W/W |
|---|---|
| Dibenzoylmethane derivative | 1–8 |
| Polyester of 2,6-naphthalene dicarboxylic acid | 1–10 |
| Octocrylene | 1–5 |
| Butyloctyl salicylate | 5–10 |
| UV-B/UV-A sunscreen | 0.5–5 |
| Isopropyl myristate | 3–7 |
| Acrylate/$C_{10\text{-}30}$ alkyl acrylate crosspolymer | 0.1–1 |
| Water | 50–90 |
| Carbomer | 0.1–0.5 |
| Phenoxyethanol()methyl paraben()ethylparaben()propyl-paraben()butylparaben | 0.1–1 |

20. A sunscreen composition including the stabilizer defined in claim 1, having the following composition:

| Chemical Name | % W/W |
|---|---|
| Dibenzoylmethane derivative | 1–8 |
| Stabilizer of claim 1 | 1–10 |
| Butyloctyl salicylate | 1–10 |
| UV-A sunscreen | 0.5–5 |
| Water | 50–90 |

* * * * *